(12) United States Patent
Loreth et al.

(10) Patent No.: US 9,480,484 B2
(45) Date of Patent: Nov. 1, 2016

(54) MODULAR SURGICAL DRIVE HUB

(71) Applicant: Smith-Nephew, Inc., Andover, MA (US)

(72) Inventors: Brian Loreth, Braintree, MA (US); Rafal Jezierski, Middleton, MA (US); Cemal Shener-Irmakoglu, Woburn, MA (US)

(73) Assignee: Smith & Nephew, Inc., Memphis, TN (US)

( * ) Notice: Subject to any disclaimer, the term of this patent is extended or adjusted under 35 U.S.C. 154(b) by 185 days.

(21) Appl. No.: 14/449,333

(22) Filed: Aug. 1, 2014

(65) Prior Publication Data

US 2016/0030057 A1  Feb. 4, 2016

(51) Int. Cl.
| | | |
|---|---|---|
| A61B 17/14 | (2006.01) | |
| A61B 17/32 | (2006.01) | |
| A61B 17/16 | (2006.01) | |
| A61B 17/00 | (2006.01) | |

(52) U.S. Cl.
CPC ..... *A61B 17/1624* (2013.01); *A61B 17/00234* (2013.01); *A61B 17/1628* (2013.01); *A61B 17/32002* (2013.01); *A61B 17/320016* (2013.01); *A61B 2017/0023* (2013.01); *A61B 2017/00296* (2013.01); *A61B 2017/00477* (2013.01)

(58) Field of Classification Search
CPC .............. A61B 17/32002; A61B 2017/00477; A61B 17/320016; A61B 17/00234; A61B 17/162; A61B 17/1624; A61B 17/1628; A61B 17/32

USPC ................... 606/167, 170, 180, 79
See application file for complete search history.

(56) References Cited

U.S. PATENT DOCUMENTS

| | | | |
|---|---|---|---|
| 4,274,414 A | 6/1981 | Johnson et al. | |
| 4,517,977 A | 5/1985 | Frost | |
| 4,844,064 A | 7/1989 | Thimsen et al. | |
| 5,376,078 A | 12/1994 | Dinger, III et al. | |
| 5,871,493 A * | 2/1999 | Sjostrom .............. | A61B 17/162 604/22 |
| 6,132,448 A | 10/2000 | Perez et al. | |
| 6,494,892 B1 | 12/2002 | Ireland et al. | |
| 2002/0058958 A1 | 5/2002 | Walen | |
| 2002/0082519 A1 | 6/2002 | Miller et al. | |
| 2003/0055404 A1 | 3/2003 | Moutafis | |
| 2003/0083684 A1 | 5/2003 | Cesarini et al. | |
| 2008/0114206 A1 | 5/2008 | Edwards | |
| 2008/0132928 A1 | 6/2008 | Jezierski | |
| 2008/0188848 A1 | 8/2008 | Deutmeyer | |
| 2013/0041392 A1 | 2/2013 | Edwards et al. | |

OTHER PUBLICATIONS

Search Report, PCT/US2015/041099, Jan. 10, 2015, pp. 5.

* cited by examiner

*Primary Examiner* — Katherine M Shi

(57) ABSTRACT

An inner assembly for a modular surgical drive hub includes a drive adapter, an inner blade adapter, and a compression member, the inner blade adapter mounted within the drive adapter and biased in a distal direction by the compression member, the drive adapter and the inner blade adapter including a key-way and a key for transmitting rotational force from the drive adapter to the inner blade adapter; wherein the inner assembly is configured to be inserted into and retained within the modular surgical drive hub. A modular surgical drive hub and a surgical instrument are described.

17 Claims, 8 Drawing Sheets

MODULAR SURGICAL DRIVE HUB

BACKGROUND OF THE INVENTION

1. Field of the Invention

The invention disclosed herein relates to tools for surgical applications, and in particular, to a hub assembly for use with a motor drive unit (MDU).

2. Description of the Related Art

A variety of disposable rotatable blade/burr styles are used in endoscopic surgery. Typically, these devices feature a drive hub that is suited for connection to a motor drive unit (MDU) via a drive adapter mechanism. Some of these devices use caps and springs through which a connection can be made to drive the device. Other drive hubs include the use of magnets to supply a preload force.

Unfortunately, some of the prior art drive hubs have designs that promote clogging, are costly to manufacture and therefore are costly to acquire. Among other things, reliance on magnets in many prior art devices has led to price volatility as well as other issues.

What are needed are designs for disposable drive hubs that are inexpensive and that operate efficiently. Preferably, the designs do not require use of magnets as part of the drive system.

SUMMARY OF THE INVENTION

In one embodiment, an inner assembly for a modular surgical drive hub is provided. The inner assembly includes a drive adapter, an inner blade adapter, and a compression member, the inner blade adapter mounted within the drive adapter and biased in a distal direction by the compression member, the drive adapter and the inner blade adapter including a key-way and a key for transmitting rotational force from the drive adapter to the inner blade adapter; wherein the inner assembly is configured to be inserted into and retained within the modular surgical drive hub.

The drive adapter may include a retaining arm configured for retaining at least one of the inner blade adapter and the compression member. The drive adapter may include a channel to receive the debris from an inner blade and to pass the debris to a slough chamber. The drive adapter may be configured to be retained within a housing of the modular surgical drive hub by tabs disposed on a sealing ring. The compression member may include a coil spring. The drive adapter may be configured to be driven by a motor drive unit (MDU). The inner blade adapter maybe configured for at least one of retention and manipulation of an inner blade. The inner blade adapter may include the key with the drive adapter including the key-way. The drive adapter may include the key with the inner blade adapter including the key-way. At least one bushing may be configured for stabilizing the inner blade within the housing. At least one bushing may be configured for providing a thrust bearing surface for an inner blade within the housing. An inner blade coupled to the inner blade adapter may include one of a cutting tool and a burring tool.

In another embodiment, a modular surgical drive hub is provided. The modular surgical drive hub includes a housing including a passage way with an outer blade affixed therein, the outer blade extending distally from the housing to a tip, the housing further including a chamber including an inner assembly; wherein the inner assembly includes a drive adapter, an inner blade adapter with an inner blade, and a compression member, the inner blade adapter mounted within the drive adapter and biased in a distal direction by the compression member, the drive adapter and the inner blade adapter including a key-way and a key for transmitting rotational force from the drive adapter to the inner blade adapter; and, the inner blade is disposed within the outer blade and extending distally to the tip of the outer blade.

The inner assembly of the modular surgical drive up may be retained within the housing by a sealing ring. The inner assembly may be one of removable and permanently sealed within the housing. A latch at least partially surrounding the housing and configured for latching with a motor drive unit (MDU) may be included. The latch may include at least one spring arm configured for the latching. The latch may include at least one guide configured to restrict rotational motion of the housing.

In another embodiment, a surgical instrument is provided. The surgical instrument includes a motor drive unit; and, a modular surgical drive hub disposed therein, the modular surgical drive hub including a housing including an passage way with an outer blade affixed therein, the outer blade extending distally from the housing to a tip, the housing further including a chamber including an inner assembly; wherein the inner assembly includes a drive adapter, an inner blade adapter with an inner blade, and a compression member, the inner blade adapter mounted within the drive adapter and biased in a distal direction by the compression member, the drive adapter and the inner blade adapter comprising a key-way and a key for transmitting rotational force from the drive adapter to the inner blade adapter; and, the inner blade is disposed within the outer blade and extending distally to the tip of the outer blade.

The surgical instrument may include one of a cutting tool and a burring tool.

BRIEF DESCRIPTION OF THE DRAWINGS

The features and advantages of the invention are apparent from the following description taken in conjunction with the accompanying drawings in which.

DETAILED DESCRIPTION OF THE INVENTION

Disclosed herein are methods and apparatus for providing disposable modular surgical drive hub. The drive hub assemblies are configured to be driven by existing motor drive units (MDU), and to power rotating blades and/or burrs.

Generally, the design for the modular surgical drive hub includes a molded adapter that encompasses an outer blade. A combined slough chamber and drive adapter creates a modular solution to provide spring force and driving torque. An inner blade or burr with an over-molded drive tang is inserted into the slough chamber and aligned with an integrated drive slot.

This compact design provides an integrated drive mechanism residing internally within an adapter body and includes an unobstructed flow path. This offers flexibility for use of differently sized blade/burr configurations while making use of the same basic components and spring.

In one embodiment, the modular surgical drive hub includes a molded polymeric adapter hub encompassing an outer blade. The adapter hub can be used for blades or burrs and accepts a low friction bushing to provide stability for blades and retention for burrs. The outer blade may be over-molded or heat staked into the adapter hub. An inner blade or burr is over-molded with a drive tang and is insertable into a modular slough chamber and spring-loaded drive hub. The inner blade or burr assembly is inserted into the outer blade through the hub adapter. Once inserted, the assembly is held in place by symmetrical tabs on a sealing ring. In the burr configuration, the low friction bushing provides restraint for axial motion out of the proximal end. A user-depressible latch provides for mounting of the device into a handset.

The design permits the modular surgical drive hub to be compact and to offer an unobstructed flow-path through the inner blade. The modular surgical drive hub is easily configured to different blade and burr diameters and styles.

In some embodiments, alternative geometries are used as drive tangs. Alternative drive tangs may be square, hexagonal or diamond shaped, or of any other shape deemed suitable. Alternative spring types may be used. Alternative spring types may include flat form, wire form, volute, torsion or of any other type deemed suitable. A retaining feature may be added to render the device completely tamper proof.

Advantageously, this design eliminates the need for internal over-molded magnets for providing a retention force. Blade and burr configurations may be easily adapted using the same molded components. The internal flow-path is unobstructed, minimizing the possibility of clogging. Without over-molded magnets, costs associated with magnet pricing volatility and licensing issues are eliminated, as well as processing issues associated with insert molding of magnets.

Figure 1:
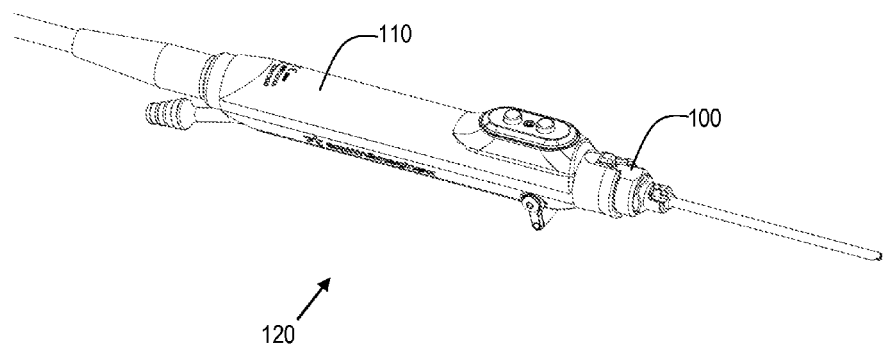
FIG. 1 is an isometric diagram depicting a surgical instrument.

Turning now to FIG. 1, there is shown an exemplary embodiment of a surgical instrument 120. The surgical instrument 120 generally includes a motor drive unit (MDU) 110 and a modular surgical drive hub 100. The motor drive unit (MDU) 110 may be any one of a variety of motor drive units (MDU) 110. Generally, the modular surgical drive hub 100 is configured to mate with existing embodiments of the motor drive unit (MDU) 110. Examples of motor drive units (MDU) 110 are provided in greater detail in FIG. 2.

Figure 2A:
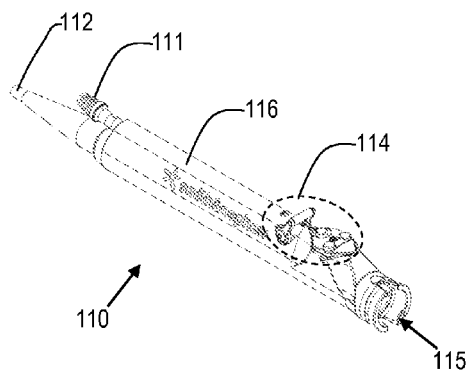
FIGS. 2A and 2B, collectively referred to herein as FIG. 2, are isometric diagrams depicting embodiments of motor drive units.
Figure 2B:
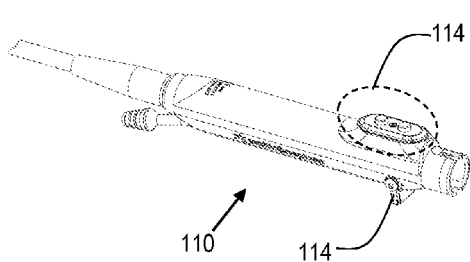

Referring to FIG. 2, there are shown exemplary embodiments of motor drive units (MDU) 110. In FIG. 2A, the motor drive unit (MDU) 110 includes a body 116. The body 116 includes components such as a motor, circuitry, tubing, switching and other such components. Generally, the motor drive unit (MDU) 110 is supplied with power through the power supply 112. Suction is provided to the motor drive unit 110 through suction supply 111. The user will control the motor drive unit (MDU) 110 through manipulation of user controls 114. In the embodiment shown in FIG. 2B, the motor drive unit (MDU) 110 includes user controls 114 that are at least partially distributed about a circumference of the body 116.

The motor drive unit (MDU) 110 may be driven electrically, hydraulically or by other systems as deemed appropriate. Additionally, the motor drive unit (MDU) 110 may include an irrigation supply (not shown). Generally, the irrigation supply provides irrigation fluid useful for irrigating a cutting site. That is, the irrigation fluid is useful for suspending cutting debris such that the debris is easily picked up with suction. Once the debris is suspended in the irrigation fluid, the debris may be easily moved through the unobstructed flow path for ultimate disposal or sampling. Other components useful with surgical instruments 120 of the type shown generally, may be included.

Figure 3:
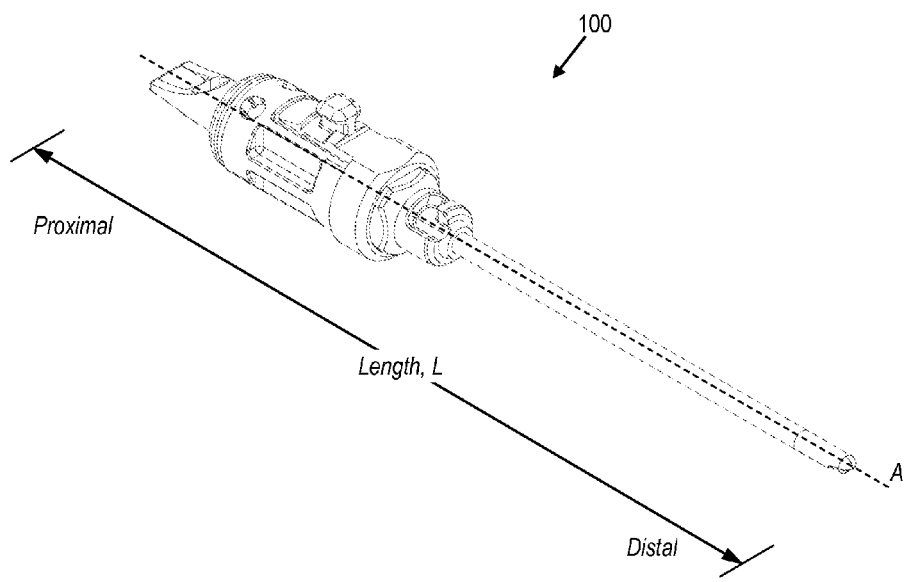
FIG. 3 is an isometric diagram depicting an embodiment modular surgical drive hub according to the teachings herein.

Referring now to FIG. 3, an embodiment of the modular surgical drive hub 100 is shown. Generally, the modular surgical drive hub 100 is configured to fit within the receiving area 115 of a given motor drive unit (MDU) 110 and to be reliably retained therein during use of the surgical instrument 120. Accordingly, each embodiment of the modular surgical drive hub 100 may exhibit a particular geometry, appearance and other such features as are necessary for fitting into a particular motor drive unit (MDU) 110 and accommodating the functions and operations as described herein.

Generally, the modular surgical drive hub 100 is easily placed into the receiving area 115. For example, with the motor drive unit (MDU) 110 in one hand and the modular surgical drive hub 100 in the other hand, the user may simply insert the modular surgical drive hub 100 into the receiving area 115 and then latch the modular surgical drive hub 100 into the motor drive unit 110.

Merely as a matter of convention, and for purposes of discussion herein, portions of the surgical instrument 120 that are closer a user (i.e., a surgeon) are referred to as "proximal," "proximate" or "proximally oriented" and by other similar terms. Aspects of the surgical instrument 120 that are further away from the user are referred to as "distal" or "distally oriented" and by other similar terms. Such terminology is not to be construed as requiring any particular orientation of the components discussed herein. For purposes of discussion, a longitudinal axis, A, has been drawn through an imaginary centerline of the modular surgical drive hub 100.

Figure 4:
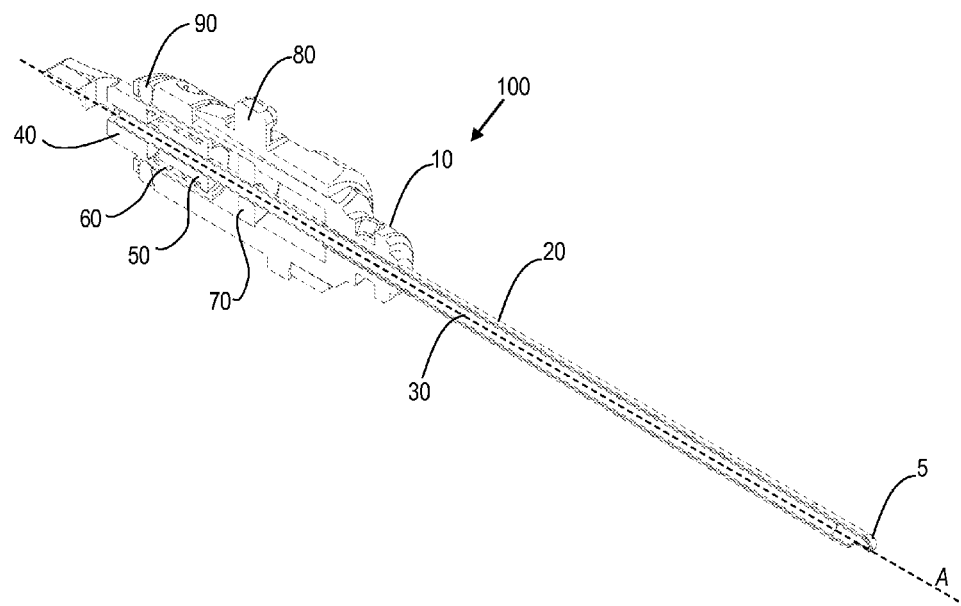
FIG. 4 is a cutaway isometric diagram of the embodiment depicted in FIG. 3.

Referring now to FIG. 4, a cutaway diagram of the embodiment depicted in FIG. 3 is shown. FIG. 4 provides an introduction to various components within the modular surgical drive hub 100. Aspects of the various components are described further herein in greater detail.

Generally, the modular surgical drive hub 100 includes a housing 10. The housing 10 includes a passage way from which an outer blade 20 extends in a distal direction. The outer blade 20 terminates at a tip 5. The proximal end of the outer blade 20 is fixed to the housing 10.

The outer blade 20 includes an inner passage way within which inner blade 30 is disposed. The inner blade 30 extends from the tip 5 in the proximal direction, into the housing 10 and beyond a proximal end of the outer blade 20. The inner blade 30 emerges from within the outer blade 20 and extends through bushing 70, inner blade adapter 50 and into drive adapter 40. Generally, the inner blade adapter 50 is surrounded by and biased in a distal direction by compression member 60. The components disposed within the housing 10 are retained in place by sealing ring 90. Surrounding the housing 10 is latch 80. Aspects of these components are discussed in greater detail below, and with reference to FIGS. 5 through 15.

Figure 5A:
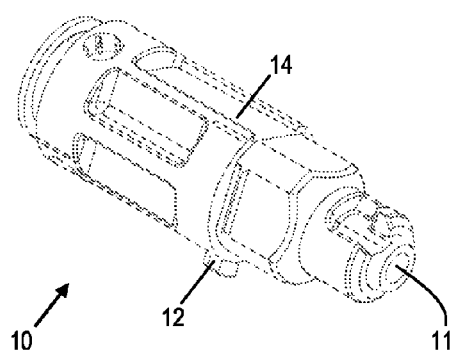
FIGS. 5A, 5B and 5C, collectively referred to herein as FIG. 5, are isometric diagrams of a housing for the modular surgical drive hub, wherein FIG. 5C provides a cutaway view.

Referring now to FIG. 5, aspects of an embodiment of the housing 10 are shown. In FIG. 5A, an exterior of the housing 10 is shown. Generally, the housing 10 is a hollow device that includes a passage way 11 the distal end for retention of the outer blade 20. A bay 14 is included on the exterior of the housing 10 for the latch 80. Generally, the bay 14 provides room for depression of a spring arm of the latch 80, thus permitting the modular surgical drive hub 100 to be inserted into the receiving area 115 of the motor drive unit 110. Also disposed on the exterior of the housing 10 is at least one guide 12. The guide 12 provides for alignment with the receiving area 115 of the motor drive unit 110. The guide 12 further ensures rotational stability of the modular surgical drive hub 100 during use. That is, the guide 12 ensures that the housing 10 does not spin when torsional force is applied to the modular surgical drive hub 100.

Figure 5B:
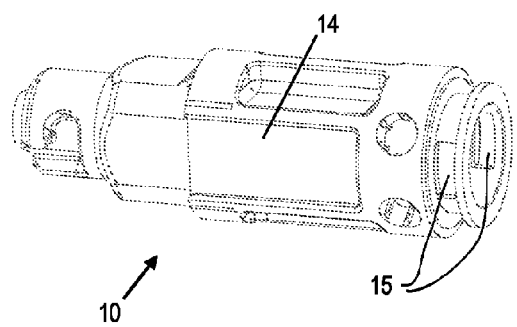

As shown in FIG. 5B, the housing 10 includes a generally open proximal end. The open proximal end provides for loading of components into the housing 10. The latch 80 and sealing ring 90 are mounted first, then the inner assembly is inserted into the open proximal end of the housing 10. The housing 10 may include at least one thruway 15. Each thruway 15 provides for improved retention of the sealing ring 90. That is, the sealing ring 90 may include complimentary features such as tabs for insertion into each one of the respective thruways 15.

Figure 5C:
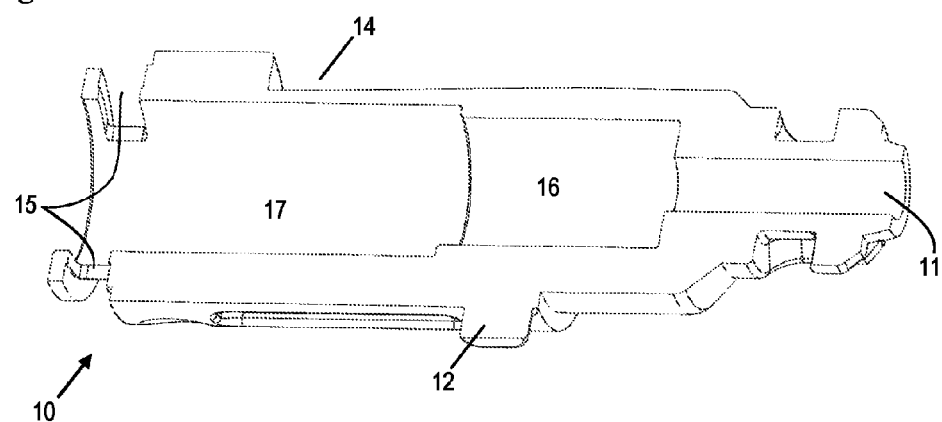

As shown in FIG. 5C, the housing 10 may include at least two chambers for housing of the components of the modular surgical drive hub 100. A forward chamber 16 has a lesser diameter than the rear chamber 17. In some embodiments, the forward chamber 16 is omitted, and the passage way 11 extends to the rear chamber 17. When assembled, the drive adapter 40, compression member 60, inner blade adapter 50, and bushing 70 are disposed within the rear chamber 17. An exemplary assemblage of these components is described in greater detail below.

Figure 6:
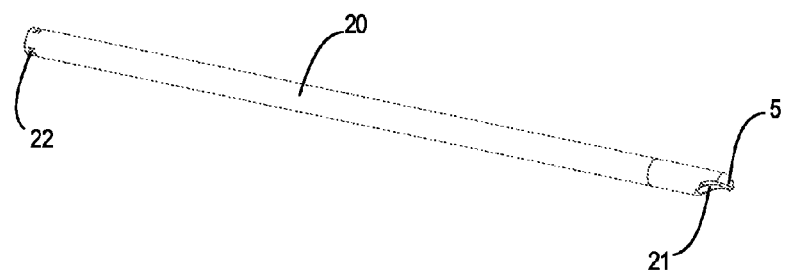
FIG. 6 is an isometric view of an outer blade.

Referring now to FIG. 6, an embodiment of the outer blade 20 is shown. The outer blade 20 is hollow such that the inner blade 30 may be inserted into the outer blade 20. In this example, the outer blade 20 terminates at the tip 5 at the distal end. The tip 5 includes a cutting window 21. A proximal end of the outer blade 20 is open to enable insertion of the inner blade 30. Generally, the inner blade 30 is also hollow along a length thereof.

Once assembled, the outer blade 20 is generally affixed to the housing 10. The outer blade 30 may be affixed by being heat-staked into the housing 10. The housing 10 may be over-molded onto the outer blade 30. Any other techniques deemed appropriate for bonding the housing 10 and the outer blade 30 may be used.

Figure 7A:
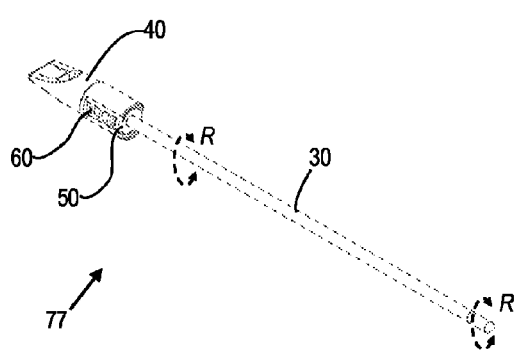
FIGS. 7A and 7B, collectively referred to herein as FIG. 7, are isometric diagrams depicting components within the modular surgical drive hub, wherein FIG. 7B provides a cutaway view.
Figure 7B:
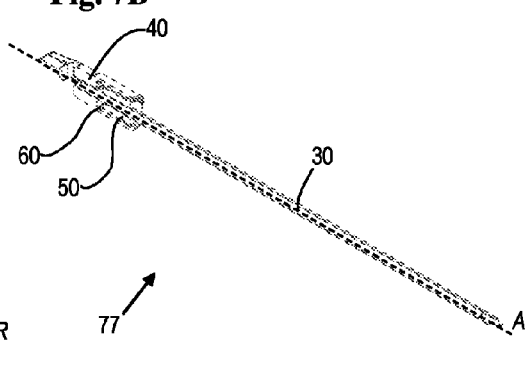

Referring now to FIG. 7, aspects of an inner assembly 77 are shown. Generally, the inner assembly 77 includes: the drive adapter 40, the compression member 60, the inner blade adapter 50, and the inner blade 30. Generally, the inner assembly 77 is configured to rotate along a rotational axis, R, when driven by the motor drive unit (MDU) 110. The inner assembly 77 may rotate in a forward direction or a reverse direction (that is, clockwise or counterclockwise). In some embodiments, rotation of the inner assembly 77 may be pulsed. In general, rotation of the inner assembly 77 is controlled by the motor drive unit (MDU) 110 as deemed appropriate. Note that FIG. 7B provides a cutaway view of the embodiment shown in FIG. 7A.

As may be seen in FIG. 7B, the inner blade 30 generally extends through the inner blade adapter 50 and into the drive adapter 40. The inner blade adapter 50 is disposed within the drive adapter 40, and biased into the distal direction by the compression member 60. Each of the foregoing components within the inner assembly 77 are described now in greater detail.

Figure 8A:
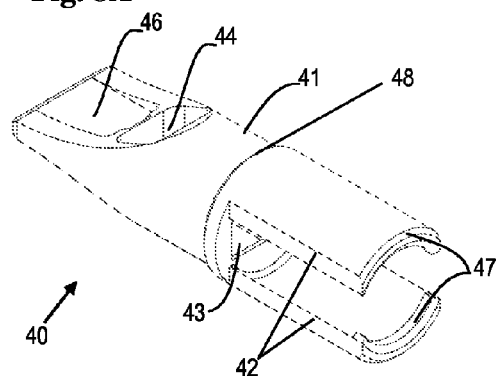
FIGS. 8A, 8B and 8C, collectively referred to herein as FIG. 8, are isometric diagrams of a drive adapter, wherein FIG. 8B provides a cutaway view.
Figure 8B:
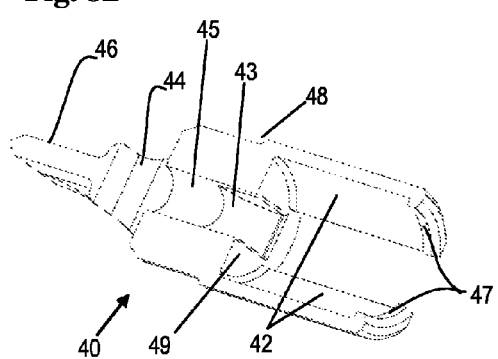
Figure 8C:
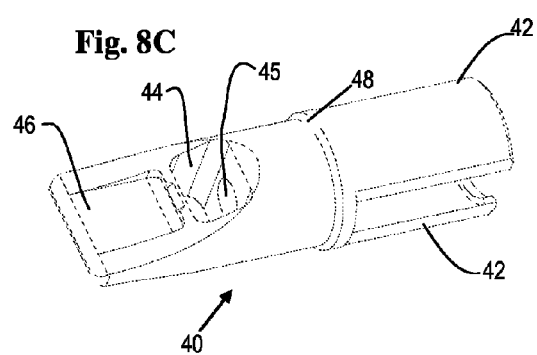

Turning to FIG. 8, aspects of the drive adapter 40 are shown. The drive adapter 40 is generally cylindrical such that it may be rotated within the housing 10. The drive adapter 40 includes a hollow body 41. Extending distally from the hollow body 41 are at least two retaining arms 42. During assembly, the retaining arms 42 may be flexed outwardly from a longitudinal axis (parallel to the axis of rotation) of drive adapter 40. Accordingly, the compression member 60 and inner blade adapter 50 (with or without the inner blade 30 mounted therein) may be inserted in between the retaining arms 42. Once the compression member 60 and the inner blade adapter 50 are inserted between the retaining arms 42, the retaining arms 42 are permitted to relax. When the retaining arms 42 relax, the retaining arms 42 return to their resting form depicted in FIG. 8.

Once the compression member 60 and the inner blade adapter 50 are inserted between the retaining arms 42, and the retaining arms 42 have returned to their resting position, the compression member 60 will bias the inner blade adapter 50 against a lip 47. Generally, each retaining arm 42 includes a respective lip 47. The at least one lip 47 limits motion of the internal blade adapter 50 in a distal direction, while the spring force provided by the compression member 60 ensures that the inner blade 30 remains biased in the distal direction.

Generally, volume between the retaining arms 42 receives the compression member 60 and the inner blade adapter 50, and therefore the proximal end of the inner blade 30. In some embodiments, the proximal end of the inner blade 30 abuts against the body 41 at platform 49. A key-way 43 that is disposed within the body 41 is used to transmit rotational force to the inner blade 30. When a suction force provides for sucking of debris from the distal tip, the debris is sucked through the inner blade 30, through an exit-way from the channel 45 and into slough chamber 44. Slough chamber 44 is exposed to the receiving area 115, thus providing an unobstructed flow path from the tip 5 (where cutting of tissue and generation of debris occurs) to the receiving area 115. Negative pressure within the receiving area 115 (i.e., the combination slough chamber and drive adapter) carries the debris away from the modular surgical drive hub 100 and away from the surgical instrument 120.

Generally, the key-way 43 is shaped to receive a feature of the blade adapter 50, where the feature is configured to transmit the rotational force. In the exemplary embodiments, the feature for transmitting rotational force is a key 52 (discussed below with regards to FIG. 9).

The body 41 of the drive adapter 40 has a diameter that is less than a diameter of the retaining arms 42. Accordingly, step 48 accounts for the changes in the diameter. Step 48 cooperates with the sealing ring 90 retain the drive adapter 40 within the housing 10 (as discussed further herein below with regards to FIG. 11).

The drive adapter 40 further includes a drive tang 46. The drive tang 46 is configured to mate with a particular drive mechanism provided in the respective motor drive unit 110. Accordingly, the drive tang 46 may be presented in any embodiment is appropriate for receiving and communicating mechanical energy from the motor drive unit 110. The blade design illustrated in FIG. 8 is merely one design, and provides for easy insertion and coupling with the motor drive unit 110.

Figure 9A:
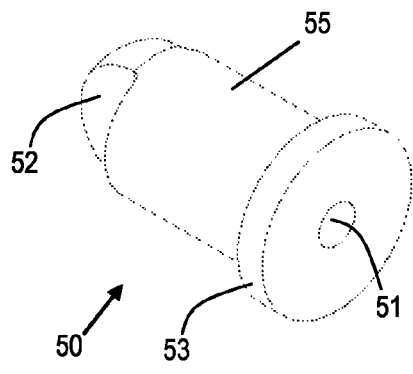
FIGS. 9A, 9B and 9C, collectively referred to herein as FIG. 9, are isometric diagrams of embodiments of inner blade adapters.
Figure 9B:
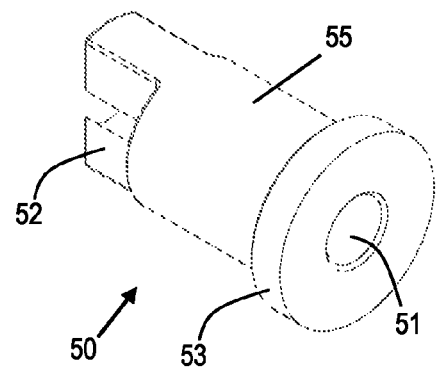
Figure 9C:
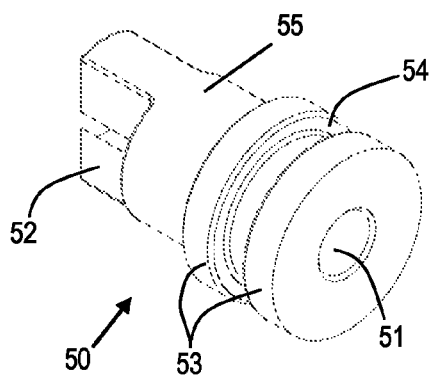

Referring now to FIG. 9, embodiments of the inner blade adapter 50 are shown. Generally, the inner blade adapter 50 is a device that provides for at least one of retention and manipulation of the inner blade 30. In embodiments disclosed herein, the blade adapter 50 includes a blade adapter body 55. Generally, the blade adapter body 55 includes an adapter passage way 51. The adapter passage way 51 is sized to receive the inner blade 30. The inner blade adapter 50 includes at least one adapter flange 53. The at least one adapter flange 53 has a greater radius then the radius of the blade adapter body 55. Accordingly, when the blade adapter 50 is inserted within the drive adapter 40, there is room for the compression member 60 (between an exterior surface of the blade adapter body 55 and the interior surface of the retaining arms 42). In the embodiment shown in FIG. 9C, a flange channel 54 is disposed within the at least one flange 53. The flange channel 54 may be incorporated to reduce weight, save on materials, and for other similar purposes.

When the inner assembly 77 is assembled, the compression member 60 provide a spring force against the body 41 and the proximal surface of the adapter flange 53.

The inner blade adapter 50 includes a feature for receiving rotational force applied by the drive adapter 40. For example, the inner blade adapter 50 may include a key 52. The key 52 may be configured to fit within the key-way 43 of the drive adapter 40. Accordingly, the key 52 provides for communication of rotational energy from the drive adapter 40 (and therefore from the motor drive unit 110).

It should be noted that the key-way 43 and the key 52 may be reversed. That is, the key-way 43 may be disposed in the inner blade adapter 50, while the key 52 is disposed in the drive adapter 40. Additionally, the key-way 43 and the key 52 may include any form of cooperative elements that provide for transmission of the rotational energy (torque) provided by the motor drive unit (MDU) 110.

In some embodiments, the inner blade 30 is over-molded by or heat staked within the blade adapter 50. Accordingly, rotational energy imparted to the blade adapter 50 is communicated to the inner blade 30.

Figure 10A:
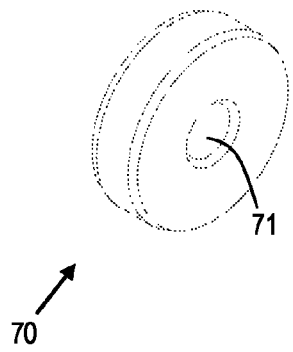
FIGS. 10A and 10B, collectively referred to herein as FIG. 10, are isometric diagrams depicting embodiments of a bushing for the inner blade.
Figure 10B:
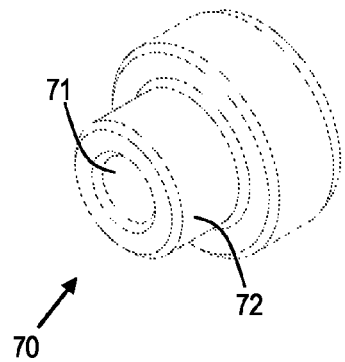

Moving in a distal direction within the housing 10, disposed beyond the distal end of the drive adapter 40 is at least one bushing 70 that includes a bushing passage way 71. The at least one bushing 70 provides for a low friction interface and to provide stability and retention for the inner blade 30. In one embodiment as shown in FIG. 10A, the bushing 70 may generally resemble a washer. In the embodiment shown in FIG. 10B, the bushing 70 may include an extension 72. The extension 72 may include a thickness having a reduced diameter.

In some embodiments, an empty volume resides between the distal portion of the drive adapter 40 and the at least one bushing 70. In some other embodiments, such as once where the bushing 70 includes the extension 72, a proximal side of the bushing 70 may be in contact with the distal side of at least one of the drive adapter 40 in the blade adapter 50, and extend to the distal side of the rear chamber 17.

Figure 11:
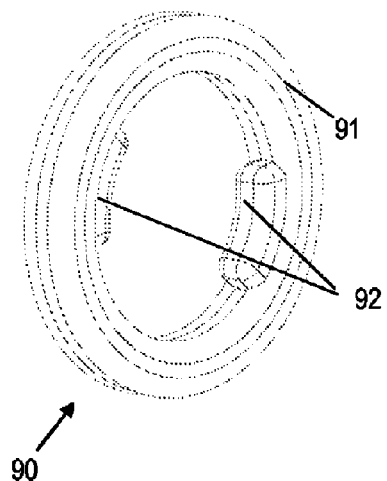
FIG. 11 is an isometric view of a sealing ring.

Referring now to FIG. 11, an embodiment of the sealing ring 90 is shown. Generally, the sealing ring 90 includes a continuous loop 91. The continuous loop 91 is generally provided as a continuous loop of elastomeric material. Included within the continuous loop 91 is at least one tab 92. The at least one tab 92 provides for mating with respective thruways 15 of the housing 10. When the sealing ring 90 is placed on the housing 10, the sealing ring 90 provides for retention of the drive adapter 40 within the housing 10. That is, the sealing ring 90 provides a restriction such that step 48 of drive adapter 40 may not pass in a proximal direction.

The sealing ring 90 may be provided as a user removable component, or may be permanently affixed to the housing 10. Accordingly, the design of the modular surgical drive hub 100 provides for disassembly, sterilization, and reuse. Alternatively the design of the modular surgical drive hub 100 provides for disposability.

Figure 12:
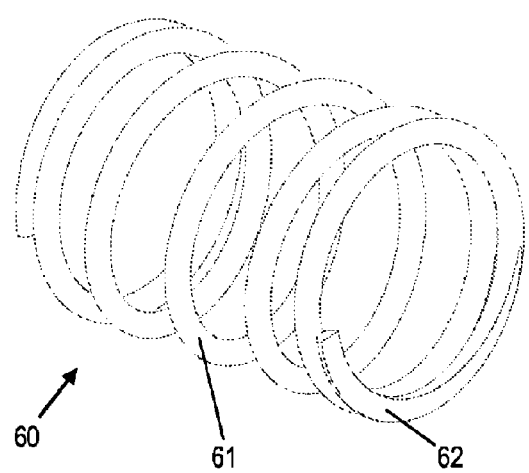
FIG. 12 is an isometric view of a spring.

Referring now to FIG. 12, an embodiment of the compression member 60 is shown. Generally, the compression member 60 may include a coil spring 61. The coil spring 61 may include a flattened edge 62. The flattened edge 62 may be provided on both a proximal end and a distal end of the coil spring 61. Accordingly, the coil spring 61 may be configured to enhance transfer of springing force. Other forms of the compression member 60 may be provided. Generally, the compression member 60 is any device that provides compressibility and a springing force.

Figure 13:
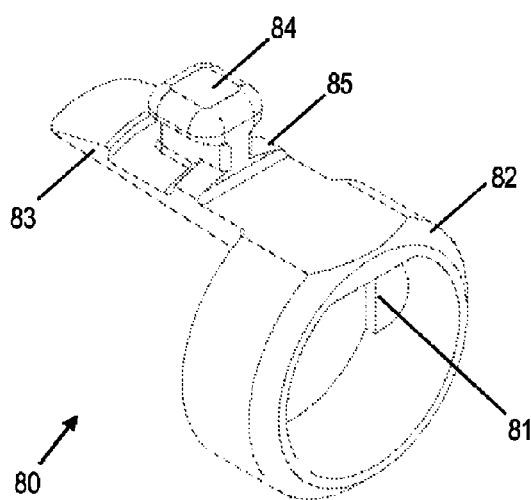
FIG. 13 is an isometric view of a latch.

Referring now to FIG. 13, an embodiment of the latch 80 is shown. Generally, the latch 80 is configured to be disposed onto an exterior of the housing 10. Included in the latch 80 is at least one interlock 81. The at least one interlock 81 is configured to securely maintain the latch 80 on the exterior of the housing 10. The at least one interlock 81 may cooperate with particular features disposed on the housing 10. In some embodiments, the latch 80 includes a latch ring 82. Generally, the latch ring 82 provides for a secure retention of the latch 80 on the housing 10. In some embodiments, the latch ring 82 is a continuous ring, and provides for encircling (i.e., surrounding) the housing 10. In other embodiments, the latch ring 82 partially surrounds the housing, and merely extends far enough to provide for the at least one interlock 81.

Generally, the latch 80 includes spring arm 83. Spring arm 83 is configured to be depressed into and fit within bay 14. Spring arm 83 may include button 84. Button 84 may provide for ergonomic user control of the spring arm 83, and as a complement to the at least one guide 12. Spring arm 83 may further include at least one latching feature 85. The at least one latching feature 85 may be configured to latch with a physical feature of the motor drive unit 110 that is disposed in the receiving area 115.

Generally, by depressing button 84, the user will also depressed spring arm 83. When spring arm 83 is depressed, the at least one latching feature 85 is moved out of the way of a retaining feature within the receiving area 115. When the button 84 is released, action of the spring arm 83 will cause the at least one latching feature 85 to latch within the receiving area 115. The at least one latching feature 85 prevents movement of the modular surgical drive hub 100 and a distal direction (and away from the motor drive unit 110), while a combination of the button 84 and the at least one guide 12 restrict rotational motion of the housing 10 of the modular surgical drive hub 100.

Figure 14:
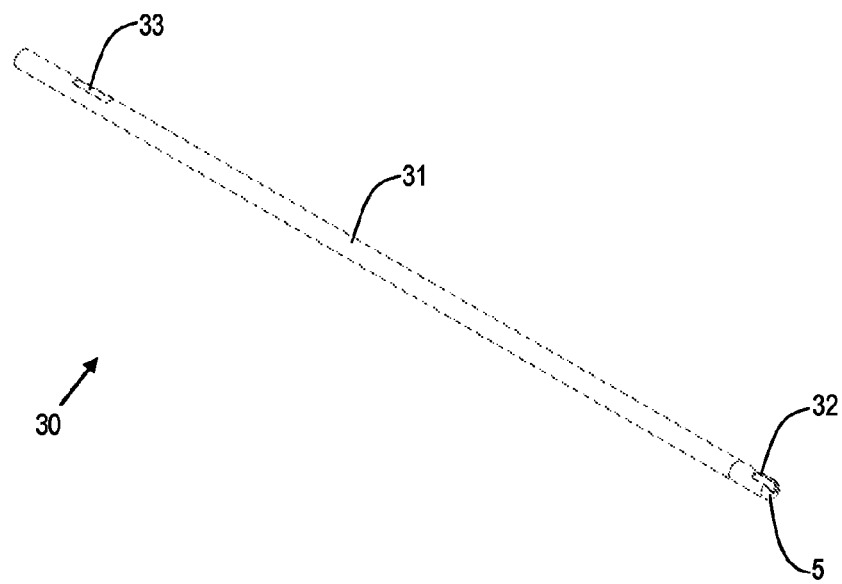
FIG. 14 is an isometric view of an embodiment of the inner blade for use as a cutting tool.

Referring now to FIG. 14, an example of the inner blade 30 is shown. In this example, the inner blade 30 includes a cutting tool 31. Generally, the cutting tool 31 is an elongated structure that fits within the outer blade 20. At the distal tip 5 of the cutting tool 31 is a cutting window 32. Generally, the cutting window 32 includes sharpened edges around a periphery of the window. Accordingly, as the inner blade 30 is rotated within the outer blade 20, the cutting window 32 will cut tissue that is in contact with the distal tip. With the application of negative pressure (i.e., suction) debris from cutting operations is sucked into the inner blade 30, down to slough chamber 44, and ultimately away from the modular surgical drive hub 100.

The cutting tool 31 may include at least one gripping feature 33. The at least one gripping feature 33. May be incorporated into the cutting tool 31 to prevent slippage between the cutting tool 31 and the inner blade adapter 50 or drive adapter 40.

Figure 15A:
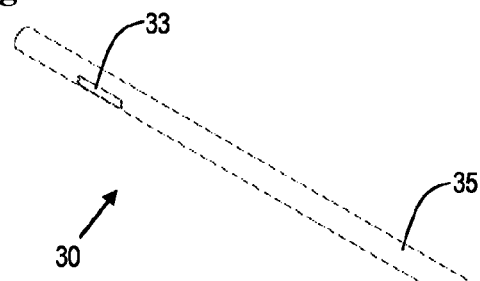
FIGS. 15A and 15B, collectively referred to herein as FIG. 15, are isometric diagrams depicting aspects of an embodiment of the inner blade for use as a burring tool; and, FIG. 16 is a cutaway schematic diagram depicting another embodiment of the modular surgical drive hub.
Figure 15B:

Referring now to FIG. 15, another example of the inner blade 30 is shown. In this example, the inner blade 30 includes a burring tool 35. Generally, the burring tool 35 is an elongated structure 36 that fits within the outer blade 20. In a distal tip of the burring tool 35 is at least one suction window 37. The at least one suction window 37 provides for application of suction during burring operations. Each embodiment of the burring tool 35 may include any one of a variety of bits 38 used for deburring operations. Each bit 38 generally has a body that is configured for mating with the elongated structure 36 while providing a particular cutting head 39. Generally, bits 38 that may be used in the burring tool 35 include, without limitation, abrader bits (as shown), barrel bits, parabolic bits, flute bits and tapered bits.

Figure 16:
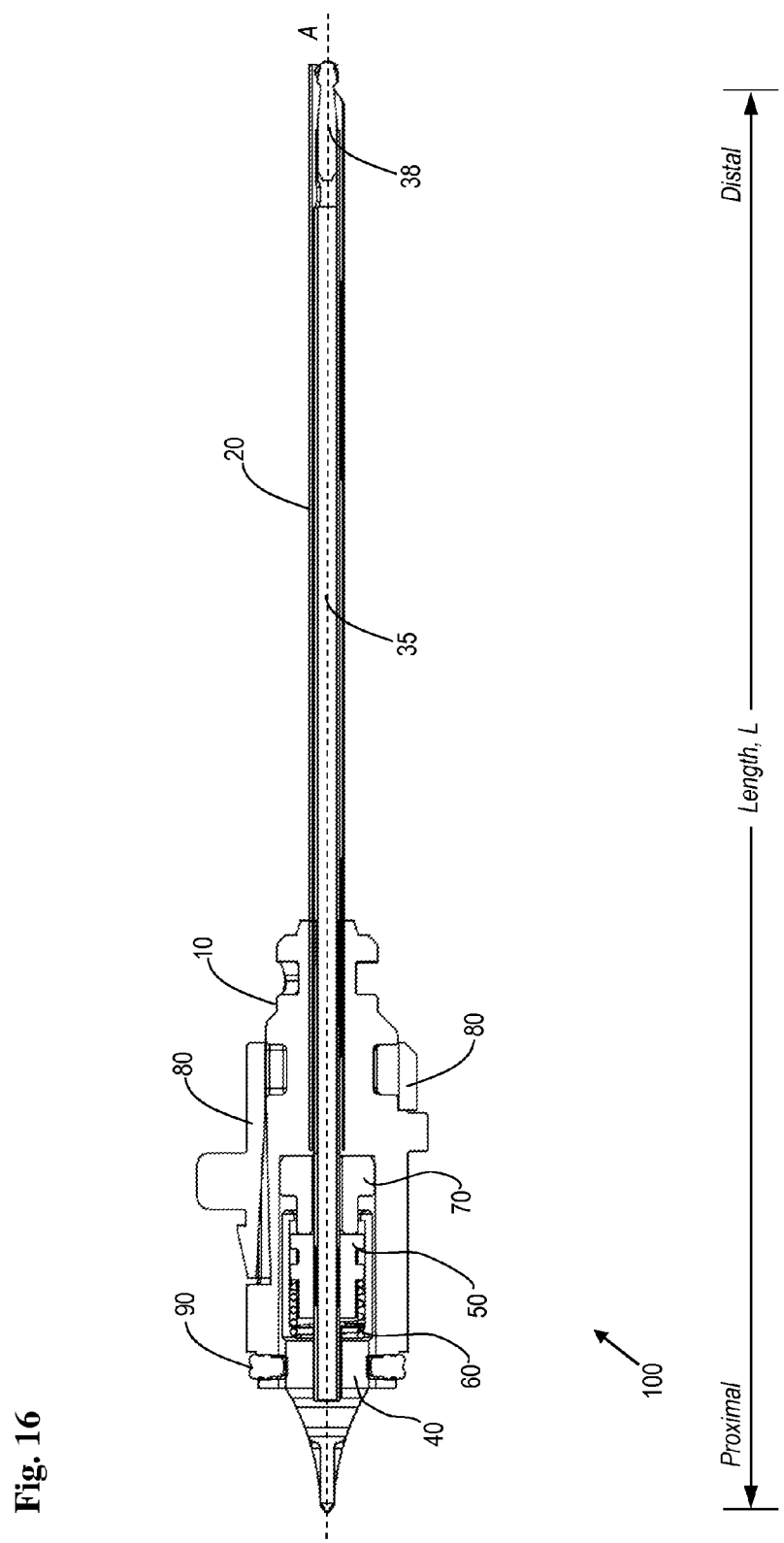

Referring now to FIG. 16, an additional embodiment of the modular surgical drive hub 100 is shown. In this example, the modular surgical drive hub 100 is configured as with the burring tool 35. As may be seen in this embodiment, the forward chamber 16 may be omitted from the housing 10. Additionally, the extension 72 of the bushing 70 may extend the into the drive adapter 40, thus pushing the inner blade adapter 50 against the compression member 60 and causing the compression member to exist in a highly compressed state.

Materials used to fabricate the modular surgical drive hub 100 and the components included therein may include any materials deemed appropriate by a user, designer, manufacturer or other similarly interested party. Exemplary materials include metal and metallic composites; plastics including polymers such as aliphatic polyamides (for example, NYLON available from DuPont of Wilmington Del.), amorphous thermoplastic polyetherimide (PEI) resins offers outstanding elevated thermal resistance, high strength and stiffness, and broad chemical resistance (such as ULTEM available from SABIC of Pittsfield, Mass.), an acetal homopolymer resin that is a highly-crystalline polymer that has high stiffness and strength (such as DELRIN available from DUPONT of Wilmington, Del.), organic thermoplastic polymers such as polyether ether ketone (PEEK), which is a colorless organic thermoplastic polymer in the polyaryletherketone (PAEK) family; polycarbonate materials; as well as rubber and other elastomeric materials.

Techniques for assembly may include snap-fitting, welding, gluing, pressing, hand assembly, pre-assembly and other such processes.

As discussed herein, the term "slough" (also spelled—and pronounced—as "sluff"), generally refers to debris generated by the inner blade and the outer blade when cutting or otherwise operating upon tissue. The term "unobstructed flow path" generally refers to a flow path away from a cutting site, and away from the modular surgical drive hub, that does not include mechanical features (such as bends and turns) or physical features (such as pressure drops) where exit of the slough may be at least partially slowed or otherwise perturbed.

When introducing elements of the present invention or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

While the invention has been described with reference to exemplary embodiments, it will be understood by those skilled in the art that various changes may be made and equivalents may be substituted for elements thereof without departing from the scope of the invention. Accordingly, any apparently limiting statements are made only with regard to a particular embodiment, and are not limiting of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A modular surgical drive hub comprising:
    a housing comprising a passage way with an outer blade affixed therein, the outer blade extending distally from the housing to a tip, the housing defines a chamber therein;
    an inner assembly disposed within the inner chamber, the inner assembly comprising:
        a drive adapter, an inner blade adapter with an inner blade, and a compression member, the inner blade adapter mounted within the drive adapter and biased in a distal direction by the compression member, the drive adapter and the inner blade adapter comprising a keyway and a key for transmitting rotational force from the drive adapter to the inner blade adapter;
        the drive adapter comprises a channel fluidly coupled to a slough chamber, the slough chamber proximally disposed with respect to the compression member; and
        the inner blade disposed within the outer blade and extending distally to the tip of the outer blade.

2. The modular surgical drive hub as in claim 1, wherein the drive adapter comprises a retaining arm configured for retaining at least one of the inner blade adapter and the compression member.

3. The modular surgical drive hub as in claim 1, wherein the drive adapter is configured to be retained within a housing of the modular surgical drive hub by tabs disposed on a sealing ring.

4. The modular surgical drive hub as in claim 1, wherein the compression member comprises a coil spring.

5. The modular surgical drive hub as in claim 1, wherein the drive adapter is configured to be driven by a motor drive unit (MDU).

6. The modular surgical drive hub as in claim 1, wherein the inner blade adapter is configured for at least one of retention and manipulation of an inner blade.

7. The modular surgical drive hub as in claim 1, wherein the inner blade adapter comprises the key and the drive adapter comprises the key-way.

8. The modular surgical drive hub as in claim 1, wherein the drive adapter comprises the key and the inner blade adapter comprises the key-way.

9. The modular surgical drive hub as in claim 1, further comprising at least one bushing configured for stabilizing the inner blade within the housing.

10. The modular surgical drive hub as in claim 1, further comprising a least one bushing configured for providing a thrust bearing surface for an inner blade within the housing.

11. The modular surgical drive hub as in claim 1, wherein an inner blade comprises one of a cutting tool and a burring tool.

12. A surgical instrument, comprising:
a motor drive unit; and,
a modular surgical drive hub disposed therein, the modular surgical drive hub comprising a housing comprising a passage way with an outer blade affixed therein, the outer blade extending distally from the housing to a tip, the housing further comprising a chamber comprising an inner assembly;
wherein the inner assembly comprises a drive adapter, an inner blade adapter with an inner blade, and a compression member, the inner blade adapter mounted within the drive adapter and biased in a distal direction by the compression member, the drive adapter and the inner blade adapter comprising a key-way and a key for transmitting rotational force from the drive adapter to the inner blade adapter;
the drive adapter comprises a channel fluidly coupled to a slough chamber, the slough chamber proximally disposed with respect to the compression member; and
the inner blade is disposed within the outer blade and extending distally to the tip of the outer blade.

13. The surgical instrument as in claim 12, wherein the inner assembly is one of removable and permanently sealed within the housing.

14. The surgical instrument as in claim 12, further comprising a latch at least partially surrounding the housing and configured for latching with the motor drive unit (MDU).

15. The surgical instrument as in claim 14, wherein the latch comprises at least one spring arm configured for the latching.

16. The surgical instrument as in claim 14, wherein the latch comprises at least one guide configured to restrict rotational motion of the housing.

17. The surgical instrument as in claim 12, wherein the inner blade comprises one of a cutting tool and a burring tool.

* * * * *